United States Patent [19]

Kowarski

[11] 4,006,743
[45] Feb. 8, 1977

[54] SYSTEM FOR CONTINUOUS WITHDRAWAL OF BLOOD

[75] Inventor: Avinoam Kowarski, Baltimore, Md.

[73] Assignee: The Johns Hopkins University, Baltimore, Md.

[22] Filed: June 17, 1975

[21] Appl. No.: 587,724

Related U.S. Application Data

[62] Division of Ser. No. 323,985, Jan. 15, 1973, Pat. No. 3,908,657.

[52] U.S. Cl. .................. 128/214 R; 128/214 B; 128/DIG. 1; 128/218 A; 128/214.4; 128/2 F; 3/1

[51] Int. Cl.² .................. A61B 5/00; A61M 1/00

[58] Field of Search ...... 128/214 R, 214 B, DIG. 1, 128/218 A, 214.4, 2 F

[56] References Cited

UNITED STATES PATENTS

| | | | |
|---|---|---|---|
| 2,183,318 | 12/1939 | Burton | 128/214 B |
| 3,496,878 | 2/1970 | Hargest | 128/214 R |
| 3,579,441 | 5/1971 | Brown | 128/214 R |
| 3,582,234 | 6/1971 | Isreeli | 417/53 |
| 3,701,350 | 10/1972 | Guenther | 128/218 A |
| 3,826,678 | 7/1974 | Hoffman et al. | 128/214 B |

Primary Examiner—Aldrich F. Medbery
Attorney, Agent, or Firm—Walter G. Finch

[57] ABSTRACT

A small, portable, constant withdrawal device is connected to tubing, including a catheter, whose internal walls are coated with heparin. The catheter is inserted intravenously through a disposable needle into a subject such as a human being. The subject may then move about for a selected period when blood is being slowly withdrawn at a prescribed rate and collected in a container within a housing supporting the device. The collected blood may then be analyzed to permit the measurement of the integrated concentration of growth hormone or any substance whose concentration in blood fluctuates widely.

In addition, a portable microdiffusion chamber is incorporated between the indwelling catheter and the extra corporal tubing and is electrically connected through a sensing probe to an associated portable sensory responsive device. This permits analyzation of the extracted blood to determine the in vivo concentration of circulating concentrations of the diffusable fraction of biological materials in the blood.

5 Claims, 7 Drawing Figures

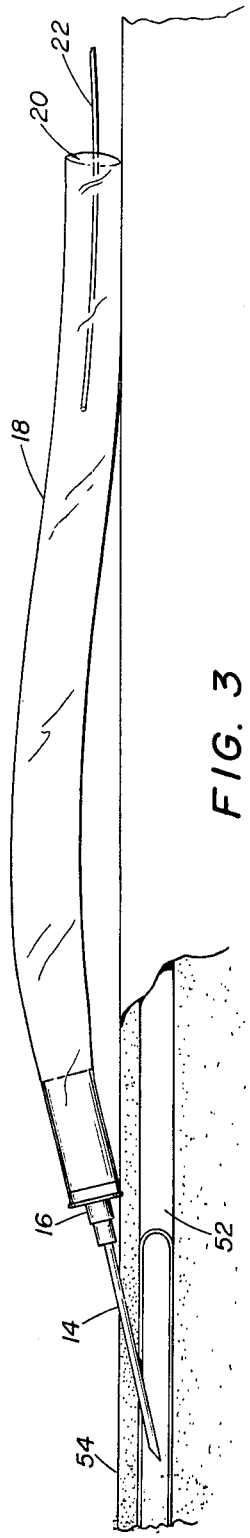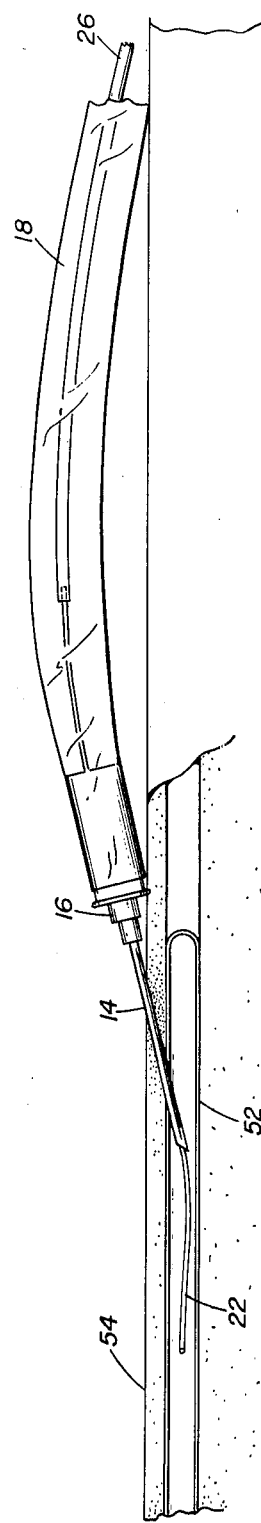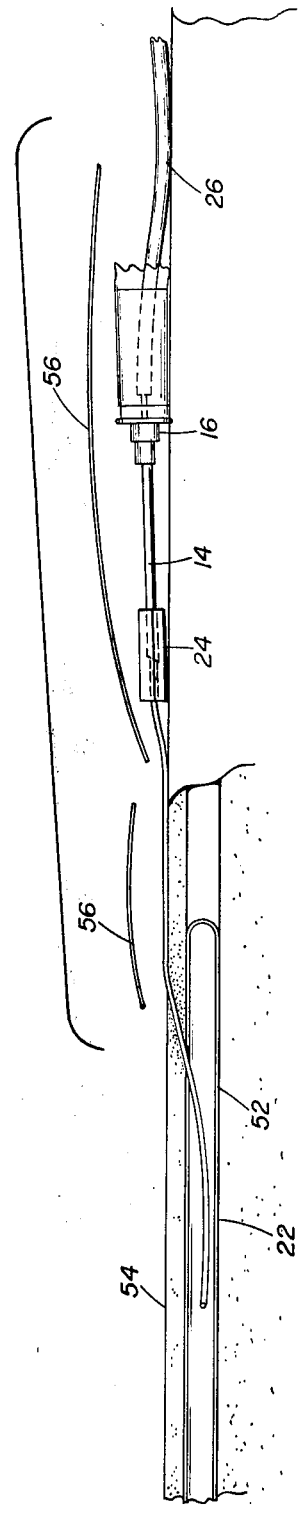

SYSTEM FOR CONTINUOUS WITHDRAWAL OF BLOOD

This is a division of application Ser. No. 323,985, filed Jan. 15, 1973 by Applicant for "System for Continuous Withdrawal of Blood" and now U.S. Pat. No. 3,908,657.

This invention relates generally to a system for the continuous withdrawal of blood and more particularly to a system for slowly and continuously drawing and collecting blood from a mobile subject for a selected period.

In order to analyze various properties of constituents contained in the blood, it is necessary that the blood be extracted from the subject. In some instances the blood concentration of a substance changes rapidly and markedly under physiological and pathological conditions. Values obtained from a single, or even multiple, blood specimens drawn in quick succession will not reflect adequately the over-all level of this substance.

For example, the integration of the concentration curves of hormones has been obtained previously by drawing numerous blood samples from a subject, measuring the concentration in each sample, and then calculating the average concentration. Use of this method results in inaccuracies in data collected and calculated as well as resulting in trauma to the subject due to the numerous blood withdrawals.

In an attempt to overcome these disadvantages, complex systems have been developed. For example, in one system, a pump withdraws blood continuously through an indwelling catheter and infuses by still another pump a heparin solution into the withdrawn blood through a smaller catheter inserted into an extra corporal portion of the indwelling catheter to prevent clotting in the extracting system. Obviously the indwelling catheter must be larger than the infusion catheter and, therefore, is limited to indwelling in veins of considerable size. Also two pumps are required. This and other similar systems require intricate arrangements and types of equipment which result in long periods of immobilization of the subject whose blood is being extracted.

Additionally, it is frequently necessary to determine the in vivo concentration of the diffusable fraction of certain biological materials in the blood. If the blood is withdrawn from the subject to measure, for example, the concentration of the diffusible part of any hormone or other material in the blood of the subject, the diffusable fraction frequently changes once the blood is outside of the body. Therefore, intravenous sensing, rather than analyzing of withdrawn blood, is necessary to obtain accurate results.

In many systems where blood is extracted and drawn through various tubes and component parts of an analyzing system, the tubes and parts can be used only for relatively brief periods without clotting of the blood therein. This reduces the opportunity for long range blood withdrawal and the attendant advantages thereof.

It becomes apparent, then, that a need exists for a non-thrombogenic system for extracting blood from a subject over a relatively long period. In addition, there is a need for a non-thrombogenic system for enabling the determination of the in vivo concentration of the diffusable fraction of biological materials in blood. Additionally, there is a need for portability of each of these systems.

It is, therefore, an object of this invention to provide a system for the withdrawing of blood from a subject over an extended, continuous period of time to permit accurate analyzation of the blood.

Another object of this invention is to provide a microdiffusion chamber sensing system for enabling external determination of the in vivo concentration of the diffusable fraction of certain biological materials in the blood.

Still another object of this invention is to provide a non-thrombogenic system which permits the continuous, slow withdrawal of blood through a single catheter over an extended period of time. Another object of this invention is to provide a nonthrombogenic system which will permit the measurement of the integrated concentration of growth hormone or any substance whose concentration in blood fluctuates widely.

Still another object of this invention is to provide a portable system for the continuous withdrawal of blood from a mobile subject.

Other objects and attendant advantages of this invention will become more readily apparent and understood from the following detailed specification and accompanying drawing in which:

FIGS. 3, 4 and 5 are pictorial views showing various steps for inserting a catheter of the system of FIG. 1 into the vein of a subject;

Figures 1, 2:
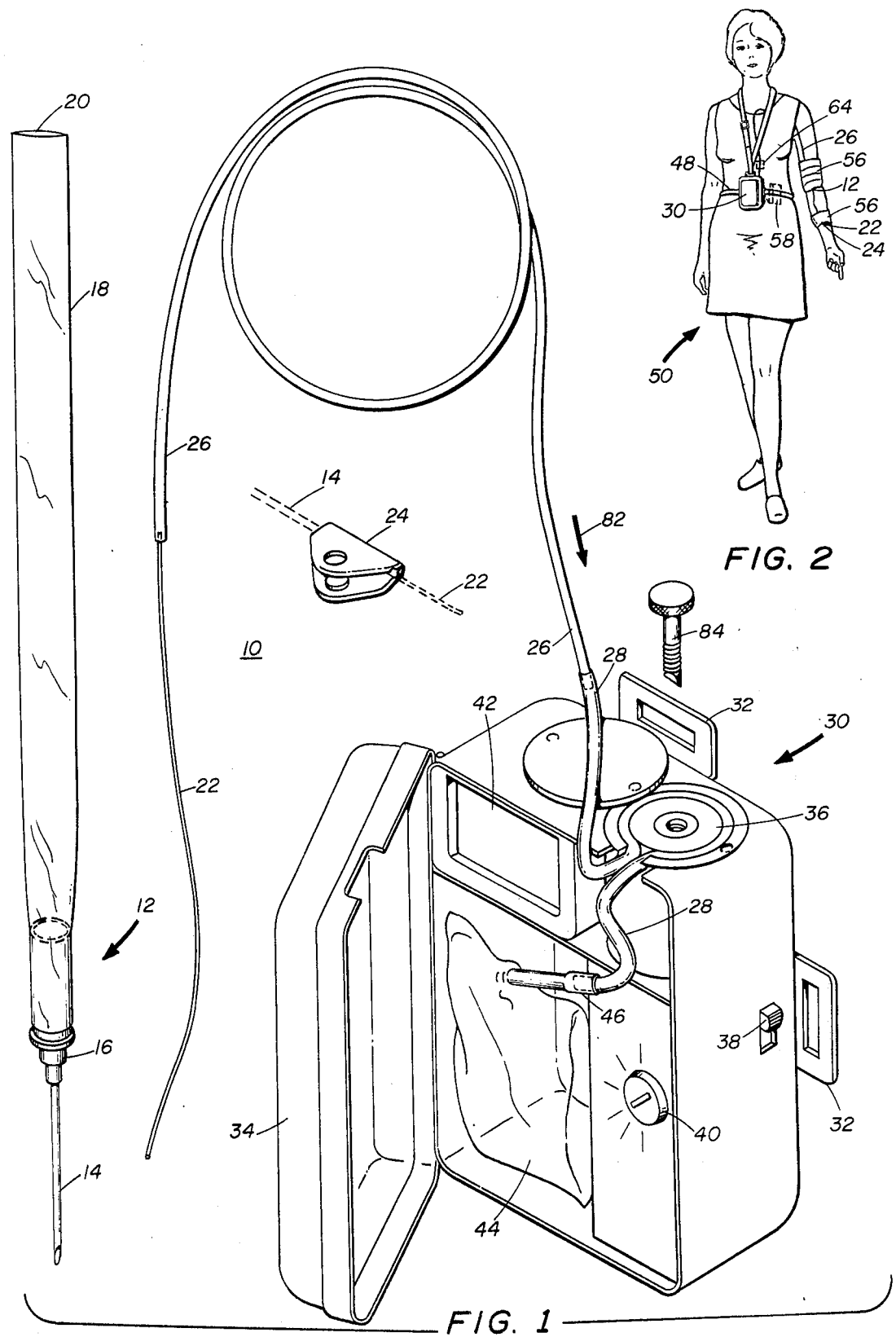
FIG. 1 is a pictorial view showing components of a system for withdrawing blood from a subject.
FIG. 2 is a pictorial view showing the system of FIG. 1 attached to a subject.

Referring now to FIG. 1, a blood withdrawal system 10 includes a disposable needle assembly 12. The needle assembly 12 includes a seventeen gauge needle 14 mounted in a needle holder 16. A plastic sleeve 18 is attached at one end thereof to an extension of the needle holder 16. The other end 20 of the sleeve 18 is open.

The system 10 further includes a nineteen gauge catheter 22 composed of a radiopaque material. The catheter 22 is free at one end and is connected to a plastic tube 26 having a larger diameter which, in turn, is connected at its opposite end to another plastic tube 28 having a still larger diameter. The connected sections of the catheter 22 and the tubes 26 and 28 are joined securely by glue.

Thereafter, the internal walls of the catheter 22 and the tubes 26 and 28 are treated to preclude clotting of blood ultimately passing therethrough. This treatment is accomplished in a two step process. Initially, by using a 50/50 mixture of toluene and petroleum ether, a 5% solution of tridodecylmethylammonium chloride is made. This solution is shaken with 200 milligrams of heparin in 100 milliliters of water. After the emulsion is separated, the supernatent portion of this mixture is drawn into the catheter 22 and the tubes 26 and 28 and left in place for two hours. After this, the solution is emptied and filtered air is drawn through the catheter 22 and the tubes 26 and 28 for 24 hours thus drying the solution that impregnated the internal walls of the catheter and the tubes. This is accomplished at room temperature. A solution of 200 milligrams of heparin in 50% methyl alcohol and 50% of water is drawn through the catheter 22 and the tubes 26 and 28 and left for three to five hours, withdrawn, and the passageway is air dried by suction as previously described for 12 hours. This impregnation-coating treatment permits a non-thrombogenic use of the catheter 22 and the tubes 26 and 28 for at least a twenty-four hour blood withdrawal period.

It is to be noted that great success has been encountered in coating tubes with very narrow internal diameters due to the drying of the wetted internal surfaces with air sucked through them by vacuum rather than the conventional method of vacuum-oven drying.

A housing 30 is formed with strap holders 32 and a hinged door 34. The housing 30 contains a rotating milking device 36 which functions as a pump or as a means for controlling the rate of withdrawal of blood from a subject 50 (FIG. 2). An ON-OFF switch 38 and a timer-control knob 40 are part of a circuit (not shown) which determines when energy from a battery 42 is applied to the milking device 36. The housing 30 and the various components contained therein are similar to a pump such as a Model ML-5-S available from Sigmamotor, Inc. of Middleport, New York. In the Model ML-5-S, the milking device 36 includes a grooved member into which a flexible tube is positioned. An eccentric roller is rotated at a prescribed rate and engages the flexible tube to milk a fluid in the tube therethrough at a prescribed rate. This is normally used to infuse the fluid into the system of a subject.

The housing 30 is formed with a compartment for containing a plastic bag 44 having a tubular port 46. An intermediate section of the tube 28 is positioned about the grooved member of the milking device 36 within the housing 30 as illustrated in FIG. 1, and fastened in this position by use of a screw 84. The remaining end of the tube 28 is inserted into the port 46 to facilitate the eventual collection of withdrawn blood. It should be noted that the plastic bag 44 is only representative of a blood collection facility and could include other facilities such as, for example, test tubes. The eccentric wheel of the milking device 36 can then be rotated at a prescribed rate to withdraw blood from the subject 50.

Referring to FIG. 2, straps 48 are used to secure the housing 30 to the subject 50. The tubes 26 and 28 are positioned through the clotting of the subject 50 so that the catheter 22 is positioned along the inside of one arm of the subject.

Referring to FIGS. 3, 4 and 5, a peripheral vein 52 in a lower portion of the arm of the subject 50 is selected and the adjacent skin area 54 is sterilized. The needle 14 is then injected into the vein 52 as illustrated in FIG. 3 and the catheter 22 is inserted into the opening 20 of the plastic sleeve 18.

As illustrated in FIG. 4, the catheter 22 is then moved through the opening of the needle 14 so that the forward end of the catheter is moved into the vein 52. As illustrated in FIG. 5, the needle 14 is withdrawn from the subject 50 and backed over the catheter 22 to the position shown. The removal of the needle 14 is accomplished in such a manner that the forward end of the catheter 22 remains in the vein 52 of the subject 50.

A plastic clamp 24 (FIGS. 1 and 5) is clamped about an exposed, intermediate portion of the catheter 22 and placed against the skin of the subject 50. Adhesive tape 56 is wrapped about the arm of the subject and the clamp 24 as shown in FIG. 2. The plastic sleeve 18 is then removed from the needle holder 16 and adhesive tape 56 is wrapped about the arm of the subject and the needle 14 and the holder. This permits complete portability of the housing 30 and the contents thereof, the indwelling catheter 22 and tubes 26 and 28. The subject 50 is free to move about and engage in normal movement.

The milking device 36 is operated by selective positioning of the ON-OFF switch 38 and the timer switch 40. The timer switch 40 can be set for a selected period of operation of the blood withdrawal system 10. For example, the system 10 can be controlled to continuously and slowly draw blood from the subject 50 at a constant rate for 24 hours. In addition, the blood can be drawn, for example, at a rate of one milliliter per hour.

The internal heparin treatment of the walls of the catheter 22 and the tubes 26 and 28 eliminate any need for heparin infusion into the withdrawn blood and, consequently, for additional pumping and infusion facilities. This enhances the lightweight aspects of the system 10 which include its portability.

The portability of the system 10 permits normal activity, including sleep, for the subject 50 while the blood is being withdrawn from the subject during the blood-withdrawing period. The blood drawn continuously over the extended period of up to 24 hours by use of the system 10 permits analyzation of the blood with more accurate results than are attainable with methods where the subject is immobilized or where there are numerous, separate blood withdrawals.

Figure 6:
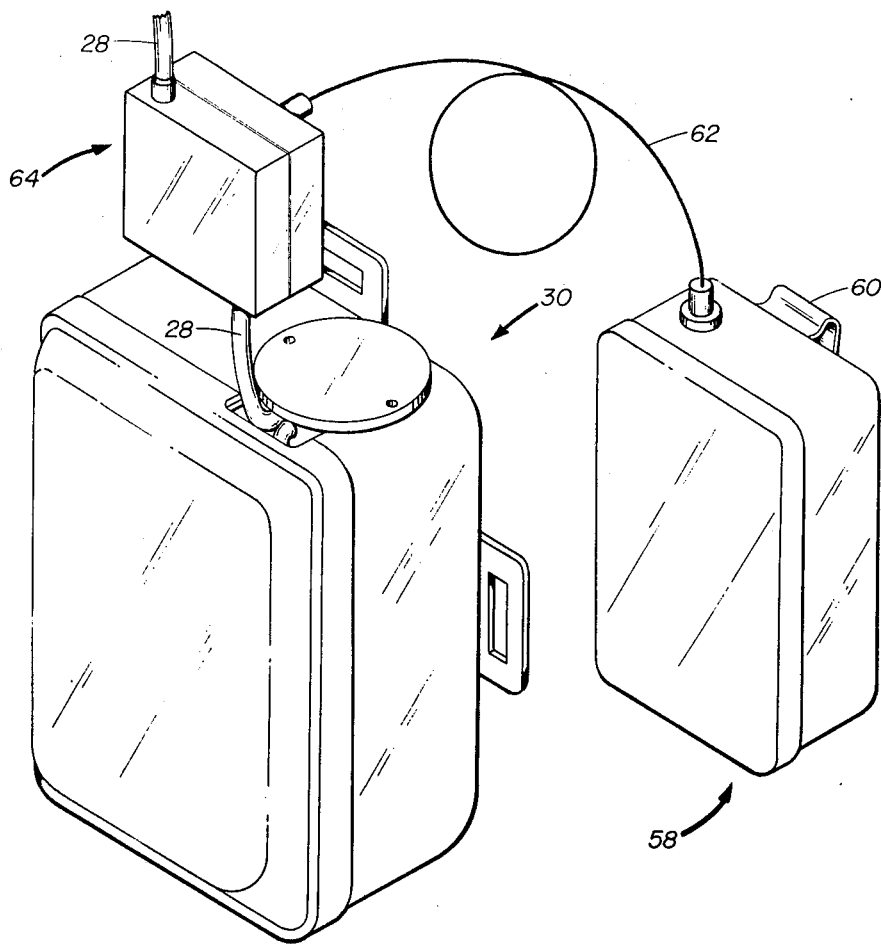
FIG. 6 is a pictorial view showing a biological material micro-diffusion and sensing system attached to the system of FIG. 1.

Referring to FIG. 6, the system 10 can be modified to include a microdiffusion chamber system 64 located between the indwelling catheter 22 and the milking device 36, and more specifically in extra-corporal tube 28. The sensor system 76 is used to sense the concentration of unbound materials in vivo and electrically send a signal over a wire 62 to a recording device 58. The sensor 62 and the recording device 58 can be, for example, a device available from Space Science Division, of Whitaker Corporation, Watham, Massachusetts. The device 58 is contained within a housing which includes a clip 60 to facilitate the attaching of the housing to the waist strap 48 as illustrated in FIG. 2. This permits portability of the microdiffusion chamber system 64 and associated equipment.

Figure 7:
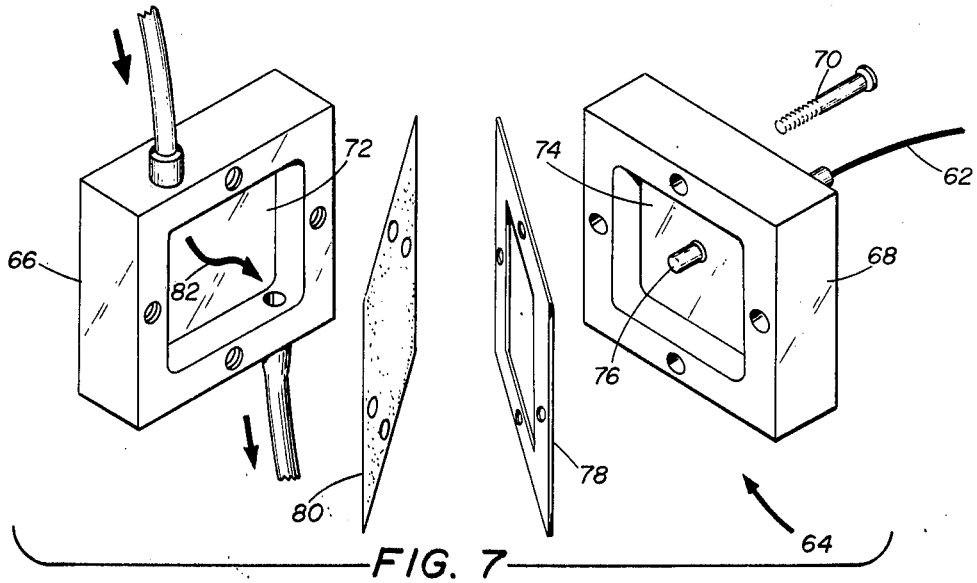
FIG. 7 is an exploded pictorial view of the micro-diffusion and sensing chamber of the biological material sensing system of FIG. 6.

Referring to FIG. 7, the microdiffusion chamber system 64 includes two plastic housing sections 66 and 68 which are joined together and held by screw fasteners such as fastener 70. The sections 66 and 68 are formed with chambers 72 and 74, respectively. A sensor probe 76, which is connected to the wire 62, extends into the chamber 74. A sealing gasket 78 and a silicone rubber diffusion membrane 80, for example, are positioned between the sections 66 and 68 such that the gasket seals the interface of the two sections and the membrane separates the two chambers 72 and 74. A cellulose-acetate membrane, if desired can be used instead of the silicone rubber membrane 80.

Since the withdrawn blood will pass through the chamber 72 as indicated by a direction-of-flow line 82 the diffusable fraction of materials in the blood will diffuse through the membrane 80 into the chamber 74. The walls of the two chambers must be treated with the two-step process previously described to establish a nonthrombogenic operation.

The probe 76 is the type referred to as a glucose sensor in an article in "Industrial Research" published on Sept. 21, 1972 and appearing on page 27. This probe 76 responds by the generation of electrical energy in relation to the concentration of materials in the blood. Previously, a probe of this type had to be inserted intravenously in order to obtain the electrical impulses necessary for measuring the concentrations of materials in the blood.

In use of the microdiffusion system 64 illustrated in FIGS. 6 and 7, one milliliter of Ringer's solution and heparin are contained in the chamber 74. As blood passes through the chamber 72, some of the heparin will diffuse through the membrane 80 to render the membrane nonthrombogenic. Also diffusable materials in the blood will diffuse through the membrane 80 into the chamber 74 and will eventually lead to equilibration of the concentration of diffusable materials in the chamber 74 and in venous blood. By use of the probe 76, detection and measuring of the concentration of such materials in the chamber occurs and permits the measurement of unbound materials in vivo. Thus, the probe 76 need not be inserted intravenously of a subject but can still detect and measure the same properties of the withdrawn blood as if the blood was within the subject. It is also possible to remove the content of chamber 74 and measure directly the concentration of the diffusable materials in it.

In summary, the system 10 permits studies on many aspects of the blood heretofore unattainable due to inaccuracies which result from previous blood collecting processes and vacillations of substances in the blood. For example, an integrated concentration of substances in the blood is that concentration of a substance determined on a specimen which has been collected over an extended period of time and which represents a mean concentration for a specified period of time. A preferable method, both in respect to scientific accuracy and in reducing trauma to the subject, is to determine an integrated concentration by analyzing the concentration of a sample of blood which results from a uniform collection of blood, minute by minute, over an extended period. The use of the system 10 to collect the blood over an extended period, for example twenty-four hours, permits the practice of the preferable method and thus provided a means of attaining more significant results in blood studies.

A number of hormones and other substances are partially bound to various proteins in blood. The biological activity of these materials is related to the concentration of the unbound moiety rather than to their total concentration. The unbound fraction in vitro is determinable by measuring the diffusion fraction. Results obtained by such in vitro methods are of limited usefulness since the studies are conducted outside the body. Also, significant changes in the equilibrium between bound and free fractions occur because of pH changes and other in vitro changes that often are unavoidable. The errors in measuring free concentrations of hormones in vitro may explain a number of inconsistencies between the concentration of the unbound biological materials, measured by presently available methods, and their known biological activity.

The development of the small catheter 22, which will permit the measurements of integrated concentrations of substances, and the development of the small, non-thrombogenic, diffusion chamber system 64, which can be inserted between the catheter 22 and the extra-corporal tube 28, will permit the determination of production rates of various substances which have not previously been determinable and a true, free fraction of the substance under study. The latter is possible because one can expect an equilibrium will be established between the diffusable fraction of materials in blood and the Ringer's solution contained in the chamber 74. In this type of study where the blood would constantly come from a vein, the results obtained for the free fraction will better reflect conditions inside the body and give more accurate data regarding interrelationship of hormones and other substances than can currently be determined using crude in vitro techniques.

It is possible to use parts of the INFUSOR SET made by Sorenson Research Company of Salt Lake City, Utah, instead of parts 14, 16, 18, and 22 described in FIG. 1.

Obviously many modifications and variations of the present invention are possible in light of the above teachings. It is, therefore, to be understood that within the scope of the appended claims the invention may be practiced otherwise than as specifically described.

What is claimed is:

1. A method for continuously withdrawing blood from a subject, comprising the steps of:
    inserting a catheter having a nonthrohmbogenic passageway therethrough into a vein of a subject;
    causing blood to move continuously from the vein into and through the passageway;
    continuously collecting said blood withdrawn through the catheter; and
    controlling the continuous withdrawal of said blood slowly from said vein at a pre-determined constant rate and for a pre-determined extended time during which the catheter is in the vein of the subject.

2. The method of claim 1 wherein the step of causing blood to move continuously from the vein into and through the passageway includes the step of continually biasing inwardly at least a portion of that portion of the catheter which is disposed externally of the subject to continuously control the rate of passage of blood through the catheter.

3. The method of claim 1 wherein the continuous withdrawal of blood through the catheter is controlled for a pre-determined extended time up to at least 24 hours.

4. The method of claim 5 wherein the anti-coagulant is heparin.

5. The method of claim 1 wherein said nonthrombogenic passageway of said catheter is so rendered by treatment thereof with an anticoagulant prior to insertion of said catheter into said vein.

* * * * *

Disclaimer 4,006,743.—*Avinoam Kowarski*, Baltimore, Md. SYSTEM FOR CONTINUOUS WITHDRAWAL OF BLOOD. Patent dated Feb. 8, 1977. Disclaimer filed July 6, 1977, by the assignee, *The Johns Hopkins University*.

Hereby enters this disclaimer to all claims of said patent.

[*Official Gazette August 23, 1977.*]